(12) United States Patent
Govro et al.

(10) Patent No.: US 10,381,115 B2
(45) Date of Patent: Aug. 13, 2019

(54) SYSTEMS AND METHODS OF ADAPTIVE MANAGEMENT OF CAREGIVERS

(71) Applicant: Sphere3, LLC, Kansas City, KS (US)

(72) Inventors: Kourtney Govro, Raymore, MO (US); Devon Kerns, Savannah, MO (US); Steven Kent Mills, Overland Park, KS (US); Kyle Evans, Faucett, MO (US); Rodney Corn, Anthem, AZ (US); Tanner Cook, Prairie Village, KS (US); Kristal Rayson, Independence, MO (US)

(73) Assignee: Intego Software, LLC, Jacksonville, FL (US)

(*) Notice: Subject to any disclaimer, the term of this patent is extended or adjusted under 35 U.S.C. 154(b) by 295 days.

(21) Appl. No.: 15/630,418

(22) Filed: Jun. 22, 2017

(65) Prior Publication Data

US 2017/0372020 A1     Dec. 28, 2017

Related U.S. Application Data

(60) Provisional application No. 62/354,866, filed on Jun. 27, 2016.

(51) Int. Cl.
| | |
|---|---|
| *G06F 19/00* | (2018.01) |
| *G16H 40/20* | (2018.01) |
| *G16H 40/63* | (2018.01) |
| *G16H 10/20* | (2018.01) |
| *G06Q 10/10* | (2012.01) |
| *G16H 40/67* | (2018.01) |
| *G06Q 10/06* | (2012.01) |

(52) U.S. Cl.
CPC .......... *G16H 40/20* (2018.01); *G06Q 10/109* (2013.01); *G16H 10/20* (2018.01); *G16H 40/63* (2018.01); *G16H 40/67* (2018.01); *G06Q 10/06398* (2013.01)

(58) Field of Classification Search
CPC ............ G06Q 50/24; G06Q 10/06393; G06Q 10/06398; G16H 40/20; G16H 10/60; G16H 50/20; G16H 50/30; G16H 10/20; G16H 50/70; G06F 19/3418
See application file for complete search history.

(56) References Cited

U.S. PATENT DOCUMENTS

| | | |
|---|---|---|
| 2010/0120000 A1 | 5/2010 | Bellamy et al. |
| 2011/0071870 A1 | 3/2011 | Gong |
| 2014/0249891 A1 | 9/2014 | Olguin Olguin et al. |

(Continued)

OTHER PUBLICATIONS

Notification of Transmittal of The International Search Report and The Written Opinion of the International Searching Authority, or the Declaration dated Oct. 12, 2017; International Application No. PCT/US2017/038789; International Filing Date: Jun. 22, 2017; Applicant: Sphere3, LLC.

*Primary Examiner* — Maroun P Kanaan
(74) *Attorney, Agent, or Firm* — Robert Schuler

(57) ABSTRACT

Systems and methods for generating a graphical interface and scheduling administrative rounds are presented. The graphical interface may present to an administrator a prioritized list of care providers based on care provider performance, care provider satisfaction, patient satisfaction, and labor data associated with the care provider. A schedule of administrative rounds to counsel the care provider may be presented to the administrator and may be based on the prioritized list, administrator and patient location, and administrator and patient schedule.

20 Claims, 6 Drawing Sheets

(56) References Cited

U.S. PATENT DOCUMENTS

2014/0379404 A1 12/2014 Bastide et al.
2015/0187038 A1 7/2015 Johnson et al.
2015/0325100 A1 11/2015 Hunter et al.

| Administrator James Jones | Date: 4/11 Time: 5:57 | | |
|---|---|---|---|
| Unit: 4 North | | | |
| ▽ Unit Care | | | |
| Patient Request Rate | Patient Induction Wait Time | Critical Request Rate | Interruption Rate |
| 1.88/hr | 1226/sec | 0.38/hr | 1.88/hr |
| Care Provider Notification % | Care Provider Response % | Care Provider Non-Notified Response % | |
| 75 | 16.67 | 0 | |
| Care Provider: Ray, Jean | | | |
| Ind Care | | | |
| Patient Request Rate | Patient Induction Unit Time | Critical Request Rate | Interruption Rate |
| 1.88/hr | 1226/sec | 0.38/hr | 1.88/hr |
| Care Provider Notification % | Care Provider Response % | Care Provider Non-Notified Response % | |
| 80 | 16 | 0 | |
| Labor Data | | | |
| Provider Performance Score 82 | Patient Satisfaction Score | PIP | See All Care Providers |

FIG. 3A

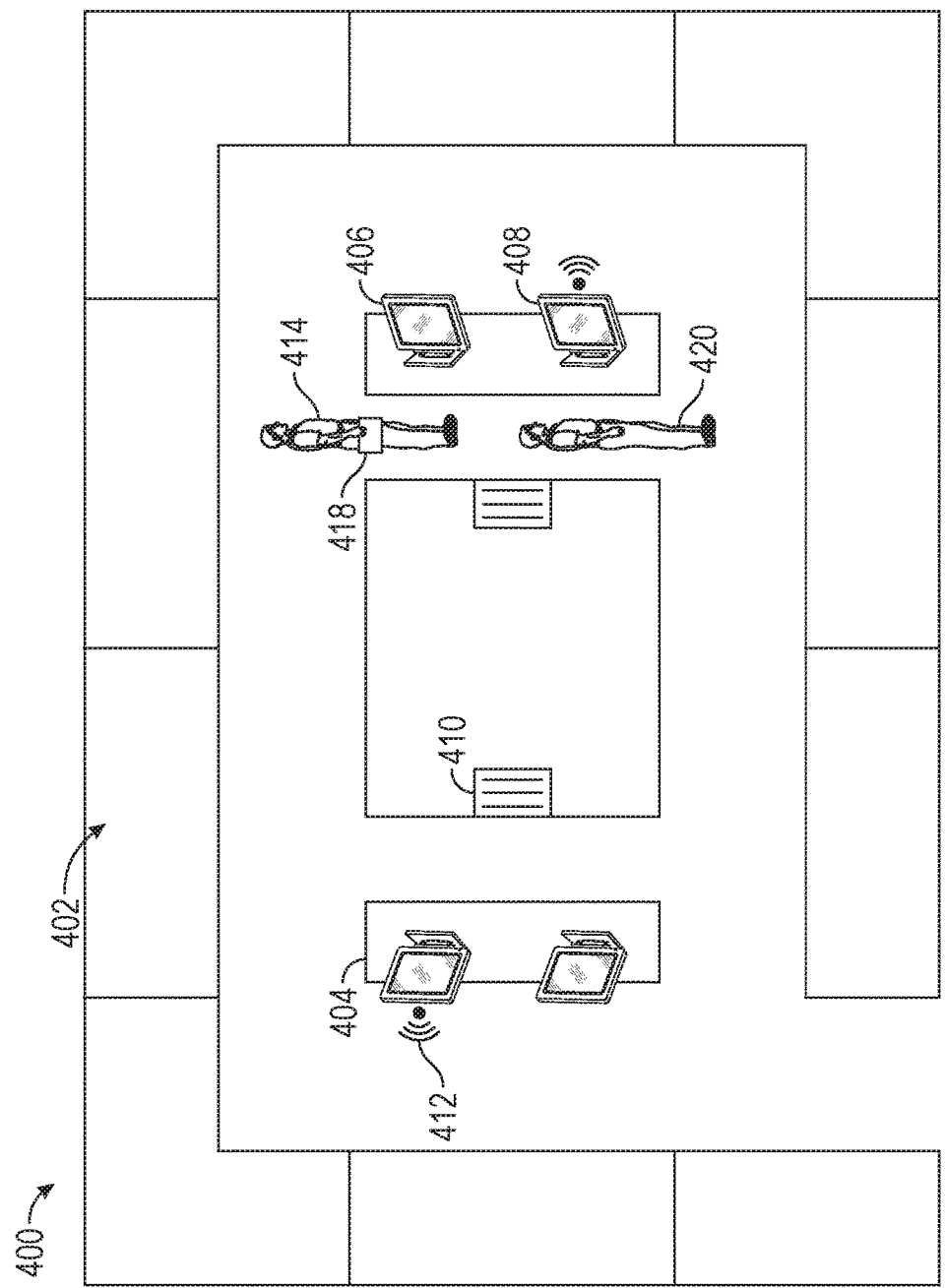

SYSTEMS AND METHODS OF ADAPTIVE MANAGEMENT OF CAREGIVERS

RELATED APPLICATION

This non-provisional patent application claims priority benefit, with regard to all common subject matter, of earlier-filed U.S. Provisional Patent Application No. 62/354,866, filed Jun. 27, 2016, and entitled SYSTEMS AND METHODS OF ADAPTIVE MANAGEMENT OF CAREGIVERS. The identified earlier-filed provisional patent application is hereby incorporated by reference in its entirety into the present application.

BACKGROUND

1. Field

Embodiments of the invention are broadly directed to computer-implemented systems and methods of tracking quantitative and qualitative data indicative of a caregiver's performance and generation of metrics to assist administrators in improving both caregiver performance and satisfaction. More specifically, embodiments of the invention provide both a hardware and software framework for collecting caregiver performance data and patient and caregiver satisfaction data that may be linked to a particular caregiver's identity, and for analyzing said data to predict the probable level of that caregiver's need for training, resources, and/or supervisory communication to improve the quality of care provided.

Further, embodiments of the invention enable the automation of a "staff contact round" and facilitate the visualization of staff members most in need of contact. A "staff contact round" or "leadership round" in this disclosure describes a visit by an administrator (such as team leads, supervisors, hospital leadership) with a caregiver to assess their current performance, well-being, state of mind, and/or satisfaction. This act is typically done on a regular basis (monthly, quarterly, yearly, or upon some other regular interval) and may be completed by a plurality or "team" of administrators. Staff contact rounds are helpful to understanding a provider's behaviors, motivations, and needs. Frequent staff contact rounds allow administrators to avoid obstacles impeding achievement of patient care performance goals even before such obstacles begin, or may at least resolve them quickly thereafter. Embodiments of the invention document the timing, details, and communication of staff contact rounds, track known issues, collect and calculate data correlations, suggest action plans for improvement, and support productive interactions between administrators and care providers.

2. Related Art

Healthcare administrators are responsible for balancing the practical needs, desires, and morale of care providers with their chief goal of providing the utmost quality of care to patients. A critical element of this balancing act is a dialogue between those in administration (team leads, supervisors, hospital leadership), and the care providers who create a patient's daily and long-term care experiences. Typically, reviews are conducted with care providers on a regular (e.g. annual, biannual) periodic basis to assess the performance, growth, requests, and complaints of care providers. This practice, however, is often not sufficiently regular contact between administrators and care providers to address problems quickly or preemptively, possibly leaving care providers feeling helpless or ignored. Issues leading to inferior patient care and a dissatisfied care staff could be avoided if administrators had tools to enable far more frequent and productive staff contact rounds.

SUMMARY

Embodiments of the invention solve these problems by providing computer-implemented structures for automating the staff contact round process by collecting data related to care being provided, patient satisfaction, provider activity, and provider satisfaction and analyzing this data to predict and prioritize care providers most in need of contact by administration for assistance or correction. Embodiments further disclose systems and methods of personalizing and interpreting such data into detailed metrics so that administrators can track the development of identified issues and care provider performance as a whole. Embodiments of the invention may produce valuable tools for improving administrator-provider communication and satisfaction, such as trend maps, priority hierarchies, questionnaires, timelines, or other tools that may be useful for improving the effectiveness and impact of a staff contact round.

In a first embodiment, a system of presenting a graphical user interface may presents rounds for a plurality of administrators. The system presents a non-transitory computer readable medium storing computer-executable instructions for execution by a processor. The steps of the computer-executable instructions may establish an identity of a care provider and an identity of an administrator and sense a location of the care provider and the administrator. Provider specific data from a plurality of data classes that may include a provider performance metric, a satisfaction score of the care provider, and a satisfaction score of a patient of the care provider may be collected. Labor data for the care provider that may be indicative of hours worked is collected and a correlation from each data class to the labor data is calculated. A correlation of the patient satisfaction score to the provider performance metric and a correlation of the provider performance metric to the provider satisfaction score may be calculated. A need of the care provider for administrative consultation based on the location of the administrator, the location of the care provider, and the provider-specific data may be determined. An administrative consultation may be scheduled and the calculated correlations may be presented to the administrator for the administrative consultation.

In a second embodiment, a method facilitating an administrative consultation between a care provider and an administrator may be presented. A location of the care provider may be sensed. Provider-specific data from a plurality of data classes that may include a provider performance metric, a satisfaction score of the care provider, and a satisfaction score of a patient of the care provider may be collected. Labor data for the care provider may also be collected and a correlation of the provider-specific data from each data class to the labor data may be calculated. A need of the care provider for administrative consultation based on the location of the administrator, the location of the care provider, and the provider-specific data may be determined. The administrative consultation may be scheduled and the calculated correlations and the plurality of data classes may be presented to the administrator for the administrative consultation.

In a third embodiment, a method facilitating an administrative consultation between a care provider and an administrator is presented. A location of the care provider and a location of the administrator may be sensed. Provider-specific data from a plurality of data classes including a provider performance metric, a satisfaction score of the care provider, and a satisfaction score of a patient of the care provider may be collected. Labor data for the care provider may be collected and a correlation of the provider-specific data from each data class to the labor data may be calculated. A correlation of the patient satisfaction score to the provider performance metric and a correlation of the provider performance metric to the provider satisfaction score may be calculated. Resources are not unlimited, so prioritizing a need of the care provider for administrative consultation based on the location of the administrator, the location of the care provider, and the provider-specific data may be determined. The administrative consultation may be scheduled and the calculated correlation may be presented to the administrator for the administrative consultation.

BRIEF DESCRIPTION OF DRAWINGS

Embodiments of the invention are described in detail below with reference to the attached drawing figures, wherein:

FIGS. 3A and 3B depict an exemplary embodiment of a graphical interface that may be presented on a display to an administrator;

FIG. 4 depicts an example location where care providers are stationed with an electronic beacon and a location indicium.

Figure 1:
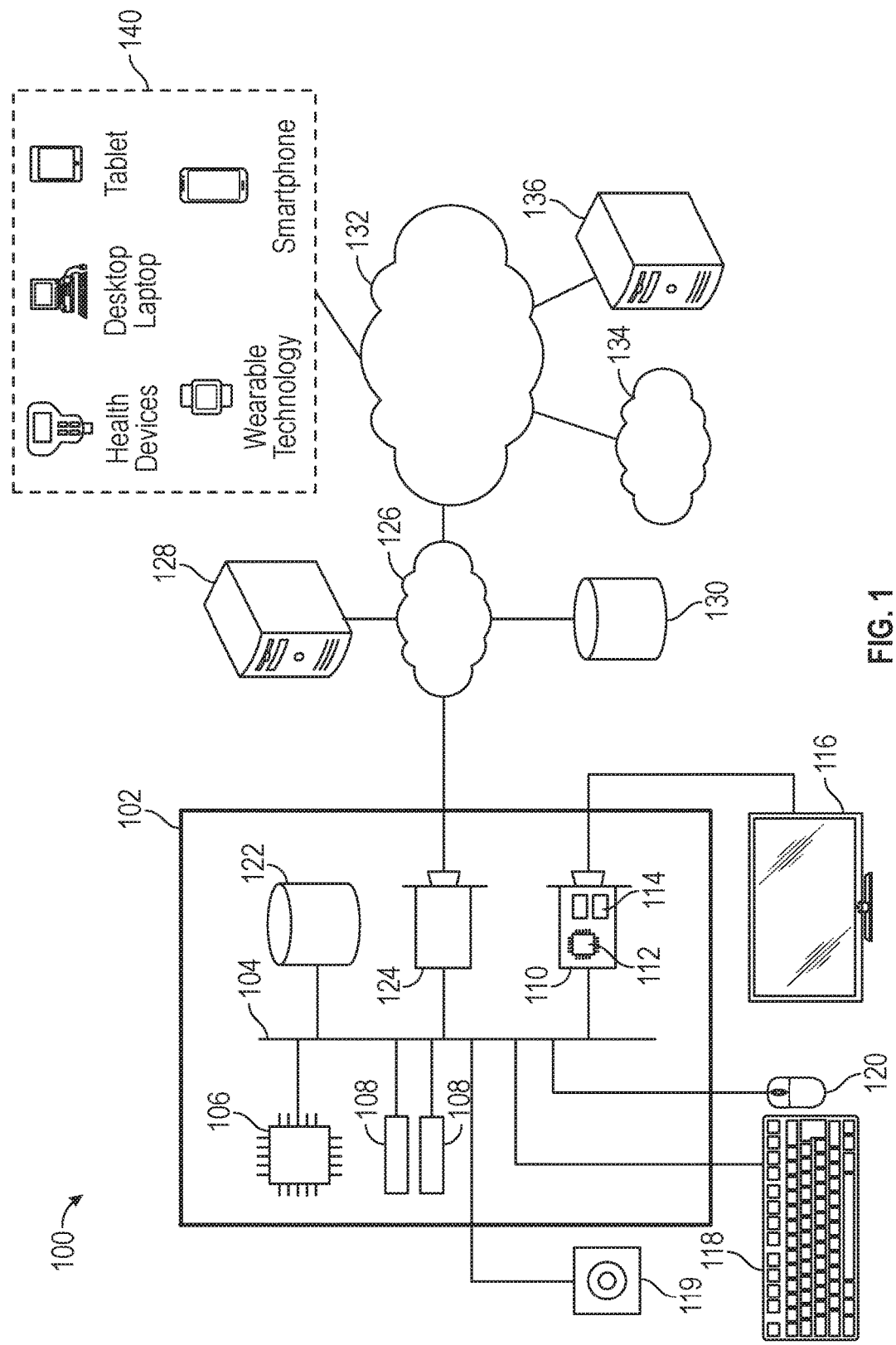
FIG. 1 depicts an exemplary hardware platform for certain embodiments of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

Embodiments of the invention are directed to systems and methods for generating a graphical interface and scheduling administrative rounds to be displayed to a user and based, at least in part, on data from care performance care metrics measuring care provided by one or more care providers, satisfaction score of the care provider, labor data of the care provider, satisfaction of patients of the care provider, and calculated correlations of the data, and providing the information to at least one administrator. Embodiments may collect a set of tasks to be performed for a population of care providers at a location of care that may be automatically sensed and relayed to an administrator to perform the tasks. Embodiments of the invention may further provide questionnaires for patients of the care providers evaluating the care that the patients received, and further providing questionnaires to the care providers determining both patient and care provider satisfaction scores. The data relating to the care providers listed above may be combined to provide administration with the information needed to evaluate the care providers and determine methods for enhancing the care provider's performance. A schedule of rounds may then be determined using the data provided and combining with other data such as, time since a last round or meeting with a care provider, schedule of care provider and an administrator, need of a care provider to be consulted based on the data collected. These examples are not intended as limiting. Embodiments of the invention may be applied in any situation in which one or more administrators have a set of consultations to be scheduled with one or more care providers.

The following detailed description of embodiments of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of embodiments of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments, but is not necessarily included. Thus, the current technology can include a variety of combinations and/or integrations of the embodiments described herein.

Turning first to FIG. 1, an exemplary hardware platform that can form one element of certain embodiments of the invention is depicted. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses or components may communicate with each other directly. Connected to system bus 104 is central processing unit (CPU) 106. Also, attached to system bus 104 are one or more random-access memory (RAM) modules. Also, attached to system bus 104 is graphics card 110. In some embodiments, graphics card 104 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments no display is present, while in others it is integrated into computer 102.

Similarly, peripherals such as keyboard 118, indicium receiver 119, and mouse 120, a location sensing component, and an identity sensing component are connected to system bus 104. A location sensing component may include a Global Positioning System (GPS) processor or any equivalent system of automatic geographical location sensing.

Additionally, a location sensing component may utilize an internal real time location indication platform including RF, IR, and/or Wi-Fi-based location indicators. An identity sensing component may comprise a biometric scanner such as a fingerprint scanner. Like display 116, these peripherals may be integrated into computer 102 or absent. In some embodiments, indicium receiver 119 may be a digital camera, barcode reader, or hardware supporting short-range wireless communication such as RFID, Bluetooth, or infrared (IR) beam communication. Also, connected to system bus 104 is local storage 122, which may be any form of computer-readable media, and may be internally installed in computer 102 or externally and removeably attached.

Computer-readable media include both volatile and non-volatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth, or Wi-Fi (i.e., the IEEE 802.11 family of standards). NIC 124 connects computer 102 to local network 126, which may also include one or more other computers, such as computer 128, and network storage, such as server 130. In some embodiments, NIC 124 may serve as part or all of a location sensing component, as further described below.

Generally, a data store such as server 130 may be any repository from which information can be stored and retrieved as needed. Examples of data stores include relational or object oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Server 130 should not be strictly viewed as a single server at a singly physical location, but rather may be comprised of a plurality of data storage servers that may be located at multiple, remote locations.

Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132. Through connection 132, the system may be communicatively coupled to devices, wearables, appliances, facility structures, and other electronic experience documentation devices, represented in FIG. 1 by element 140.

Embodiments of the invention may utilize data relating to patient data, provider performance metrics, provider labor information, and satisfaction scores collected in a wide variety of ways. Some data may be manually entered via the patient, care provider, or an administrator via a workstation, internet web portal, kiosk, application running on a wireless device, or by any other manual method. Additionally, data may be pulled automatically from previous electronic medical records or from scanned-in paper records with optical character recognition (OCR). Behavioral data is recorded directly from an "Internet of Things" including devices, sensors, monitors, and technologies used by a patient, provider, or administrator to communicate a need or activity either physically (i.e. via push of button or movement) or physiologically (i.e. from a cardiac or other monitor). Location and movement data may be extracted from sensors, monitors, and/or other various readers included in a data table. Data may be fed to the system from databases of outside sources such as labs and imaging centers. Further, health and/or behavior data can be collected from wearables, such as a pedometer, activity tracker, blood pressure cuff, or diabetic monitor. Such "wearables" may be in the form of an application running on an electronic device worn or carried by the caregiver, such as a dedicated activity tracker (e.g., a FITBIT or VIVOFIT) or a mobile device, such as a smartphone. Data from wearables may be periodically collected from a web-based cloud. Further yet, data may be transmitted to the system from larger appliances such as infusion pumps, ventilators, treadmills, electronic scales, or other general transmission methods. Embodiments of the invention may be communicatively coupled with and draw data from facility-wide structures, such as nurse call systems, interactive patient beds, and real-time location systems. The above data sources are intended only to be exemplary and are in no way meant to limit the invention. Data acquired by any means from any source may be used in the embodiments of the invention.

Data acquired through wearables, sensors, devices, and monitors is used to analyze the caregiver or provider's engagement, performance, work duration, and workload during a shift. The movements and engagements of a provider (such as a nurse, doctor, therapist, or any other care provider) are used in embodiments of the invention to measure the provider's performance. Data may be fed to the system from databases of outside sources such as labs and imaging centers. Indicators of a care provider's performance may include measurements of responsiveness to call lights, quantity of calls lights responded to, and/or escalation events beyond a care provider's response. Further, health and/or behavior data can be collected from wearables, such as a pedometer, activity tracker, blood pressure cuff, or diabetic monitor. Such "wearables" may be in the form of an application running on an electronic device worn or carried by the patient, such as a dedicated activity tracker, such as a distance-tracking smart watch, or a mobile device, such as a smartphone. These are merely examples, and are not intended to be limiting. Any measurable that helps to paint a better picture of the caregiver's workload and ability to engage with the patient may be within the scope of embodiments of the invention.

Further, measurable data collected from wearables such as a pedometer worn by a provider may be used to identify behavior patterns of activity not directly focused on direct patient contact or indirectly directed towards creating an environment of care. Data collected from questionnaires created by administrators and delivered to patients and/or care providers through an application generates critical data for measuring the effectiveness and efficiency of each care provider.

In embodiments, data from wearables may be periodically collected from a web-based cloud, such as server 130. Further yet, data may be transmitted to the system from larger appliances such as infusion pumps, ventilators, treadmills, or electronic scales. Embodiments of the invention may be communicatively coupled with and draw data from facility-wide structures, such as nurse call systems, interactive patient beds, and real-time location systems. The above data sources are intended only to be exemplary and are in no way meant to limit the invention. Data acquired by any means from any source may be used in the embodiments of the invention.

Data acquired through wearables, sensors, and monitors may be used to analyze providers' engagement and workload with one or more patients during a shift and/or across many shifts. Similar to how the behaviors of patients are measured through their movements, needs, and requests (both physical and physiological), the movements and engagements of a provider (e.g. nurse, doctor, therapist) may be used in embodiments of the invention to manage the provider's true workload as opposed to the perceived workload indicated in a medical record.

Traditionally, a provider's time is often managed by calculating an allotted amount of time to manage a patient's care using the acuity level, diagnoses, and/or symptoms of a patient. Time allocated in this standard acuity model often does not consider "non-scheduled" activities such as interruptions, walking distance, loss of equipment, and other indirect consumers of a care provider's time. Embodiments of the invention may account for these "non-scheduled" activities in addition to performing steps of the traditional time management model.

In embodiments of the invention, administrators can create questionnaires regarding experiences and/or satisfaction that may be customized to a particular patient type, demographic, and/or provider type. These questionnaires may be delivered to each respondent, whether patient or care provider, via an electronic means such as email or an application running on a computing device. The questionnaires may have a particular set of questions or may be selected randomly or semi-randomly from a large bank of questions, and may be scheduled to be released at particular times or upon particular intervals. For instance, satisfaction questionnaires may be sent to care providers every 90 days. Additionally or alternatively, one or more questions may be sent ad hoc to address specific concerns to an individual patient, care provider, unit, or group thereof. Responses to questionnaires may be linked to the identity of a particular provider, a team of providers, a patient, or may be anonymous.

Questionnaires created semi-randomly may select a predetermined number of questions from a bank of types of questions. For instance, a questionnaire for care providers may be designed to have 2 questions regarding time budgeting, 3 questions regarding communication with management, and 4 questions regarding satisfaction. The system may then randomly select the selected number of each type of question from a bank of previously written questions denoted as each type. The questionnaires are then capable of covering a wide range of specific topics while having a level of uniformity across the entire care provider staff. Examples of questions that may appear on a typical questionnaire for care providers include the following:

Do you have all the tools necessary to do your job well?
What's working well for you at the hospital?
Is there anyone you want to recognize?
Describe your best day since your last staff contact round.
Describe your worst day since your last staff contact round.
Are there staff members you enjoy working with?
What can we fix to make things better?
Is there anything you need from management?

The questions above are only exemplary and in no way limiting. The questions may be satisfaction-based and present the feelings of the care provider and/or may present requests by the care provider or suggestion. The questions may be presented in categories and/or responses may be categorized after collection to align with hospital initiatives. The results may be associated with results of all care providers and presented in the form of plots and/or graphs to provide easily recognizable trends, areas in need of improvement, and departments in need of the most attention. Results may additionally or alternatively be automatically associated with the care provider for future reference in administrative consultations.

Embodiments of the invention include systems and methods of generating graphical user interfaces presenting administrative duties to be performed based at least in part on personalized care metrics, as illustrated in U.S. Provisional Application No. 62/333,955 filed May 10, 2016, entitled CARE LOGGING UTILITY WITH PERSONALIZED METRICS, and U.S. patent application Ser. No. 15/591,523, filed May 10, 2017, and entitled PERSONALIZED USER INTERFACES PRESENTING CARE TASKS, both of which are hereby incorporated by reference in their entirety into the present application. Examples of personalized care metrics include Patient Request Rate, indicating how often the patient is needing care, Patient Interaction Wait Time, indicating how long (on average) the patient is having to wait for care, Critical Request Rate, indicating how often the patient is expressing an emergent need for care, and Interruption Rate, indicating how often the patient and subsequent "escalations" are disrupting or creating variability in the workload of a care team. These examples are not intended to be limiting. Other personalized care metrics, such as a Caregiver Response Percentage or any other advanced analysis of care provided may be employed in alternative embodiments of the invention. The personalized care metrics provide data indicative of the performance of the care provider and the phrase provider performance metric may be used interchangeably. The data representing the provider performance metric may be one of the identifiers leading to a consultation with administration. Other factors leading to and scheduling a consultation may be, but are not limited to, staff and administrator availability and schedule, time since a previous consultation, request by the care provider or the administrator, patient and/or care provider satisfaction, care provider labor data, or at the request of an outside party such as another staff member or administrator.

The application described above may be downloaded from the internet by care providers and administrators upon employment. The application may require login to an account created by the application, by the care provider, the administrator, or by a website. The account may assign one or more roles to a logged-in user, such as a type of care provider, administrator, or patient. As further discussed below, administrator accounts on the application may present to an administrator user staff contact rounding tools, issue management tools, comments, schedules, and communications.

Embodiments of the invention include an application running on computing devices described above. For purposes of this discussion, such a device will be exemplified as a smartphone, but the device could equivalently be realized as a tablet computer, PDA, smart watch, mobile PC, or any other electronic computing device capable of wireless communication. The application provides a convenient workspace for both inputting and viewing patient data as well as presenting personalized care metrics and any other data associated with a patient, care provider, and administrator. The patient, care provider, and administrator may have associated accounts for logging in and may contain both public, shareable, and confidential information.

Figure 2:
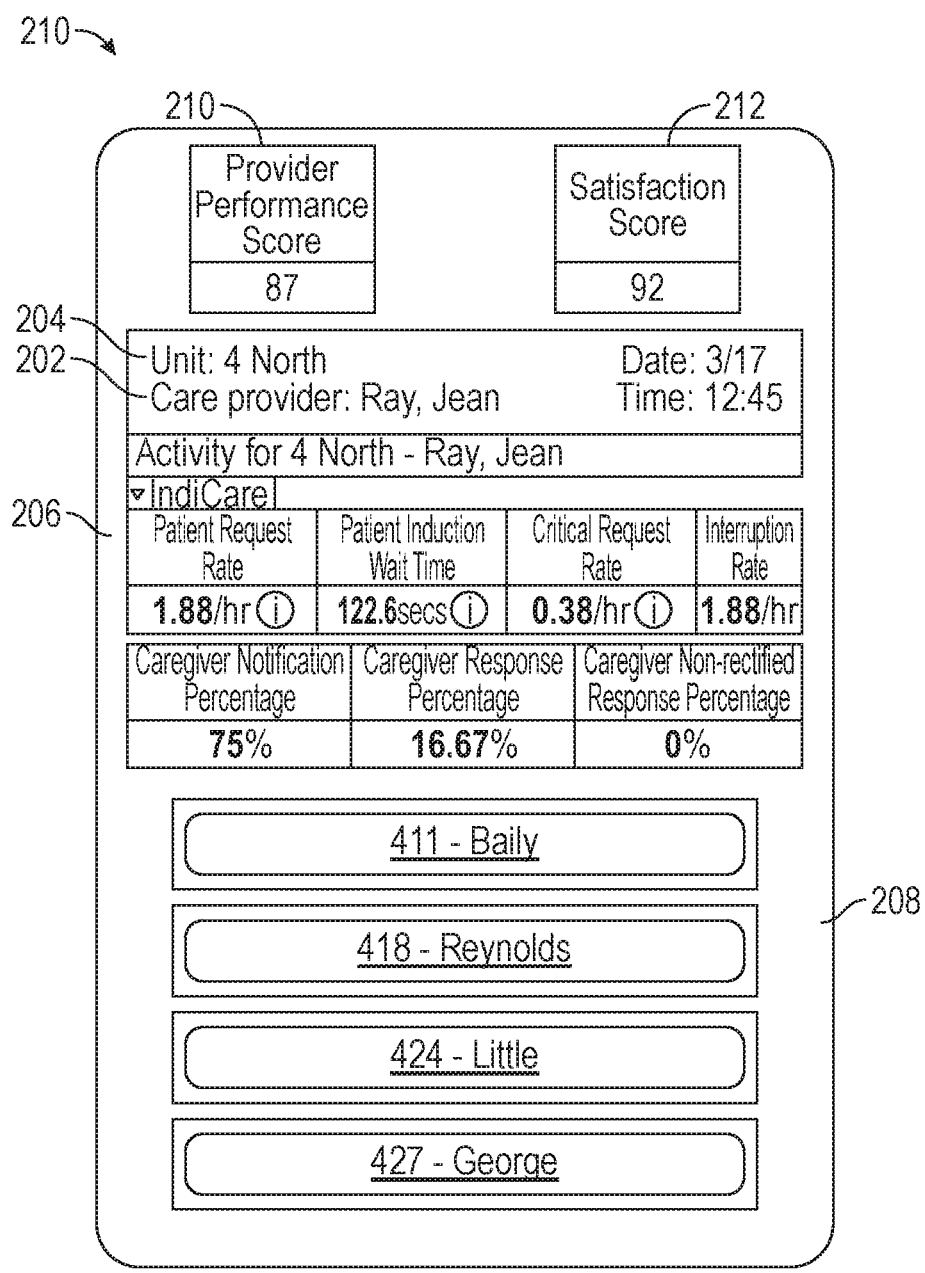
FIG. 2 depicts an example of a graphical interface that may be presented on a display to a care provider in embodiments of the invention.

In an embodiment depicted in FIG. 2, interface 200 showing reference information including the care provider's name 202 and the current location 204, as well as the date and time. Additionally, displayed interface 200 includes personalized care metrics information 206 analyzing the current and/or prior performance of the care provider 202. Displaying personalized care metrics information 206 allows the care provider 202 to be continuously aware of the level of care being provided. The accumulation of all personalized care metrics may be listed as a provider performance score 210. Additionally, a provider performance score 210 may be calculated from the provider performance metrics that allows easy reference for evaluation by the provider or an administrator. The score may also be compared to the scores of other care providers, or a total average score of all care providers.

Patient list 208 included on displayed interface 200 presents a plurality of patients requiring care from care provider 202. In some embodiments, selection of a patient from patient list 208 may display one or more tasks to be performed by care provider 202 for that patient. In embodiments, the patient list 208 may be color coded or otherwise formatted in an attention seeking manner to display urgency of care requested, an impending time for completion of a care task for the patient displayed, and/or a status of a personalized care metric for the given patient.

For example, a patient list icon for a patient that has been waiting an hour for a requested medication may be displayed red and/or flashing to indicate that the task is overdue. Further, the patient name may be displayed in specially formatted text, such as all capitals or bolding, to indicate that this patient is contributing negatively to one or more personalized care metrics for the care provider 202. Additionally, or alternatively, the device displaying interface 200 may vibrate and/or generate audible alerts of urgency or criticality of care requested, in embodiments.

Further, in embodiments of the invention, responses from questionnaires from any source may be collected for each care provider or unit to create an overall satisfaction score 212 multiple satisfaction scores, designated by source. The personal satisfaction score 212 may be calculated by the system based on weighted values of current and prior health and experience data. The satisfaction score 212 may be based on functions transforming past health and behavior parameters into satisfaction levels, and the system may update these functions as actual satisfaction data points are collected from the patient. Satisfaction scores 212 may be presented to providers or patients in any form, including a number, color code, or pictograph. Sudden changes in satisfaction score 212 may be used to identify trigger levels of health or behavior parameters, leading to a significant gain or drop in patient satisfaction. Trigger levels may further be partially or wholly based on deviations from average values in a single or across multiple parameters of health and behavior. Some values may intentionally be excluded from a patient's satisfaction score 212 so that a provider is not motivated to skew the parameter, such as pain level, in a direction that would improve the patient's satisfaction score 212. As with the activity metrics 206, the satisfaction score 212 may be displayed as an average for all patients for a care provider or all patients in a particular unit or facility. The satisfaction score 212 may also be used with other parameters, such as activity metrics 206, and questionnaires, as well as calculated performance data to calculate an overall provider performance score 210 for a care provider. The satisfaction scores 212 can then be compared with a database of information regarding care provided and activities of each provider, as well as the date of their last staff contact round, to generate tools for administrators such as a priority list of care providers or units most in need of a staff contact round. Further tools that may be generated include a color-coded heat map of care providers or units in greatest need of a staff contact round, an overall performance score for each care provider or unit, or a trend map of performance scores over time.

The above example as depicted in FIG. 2 is in no way limiting and represents one of a plurality of factors tracking and displaying data and used in evaluating care providers. The personalized care metrics, satisfaction scores, and provider performance scores, or any other evaluation information may be considered during the administrative rounds or during one on one consultations between care providers and administrators where a plurality of care providers and administrators may be present.

FIG. 3A is one example of a user interface that may be generated in embodiments of the invention providing rounds to an administrator, displaying a list of care providers in need of a consultation by the administrator 302, James Jones. The administrator 302 may receive an automatic alert notifying the administrator that a round, or a particular consultation, is scheduled. Illustrated in FIG. 3A is a displayed interface 200 showing reference information including the administrator's name 302 and the current location 304, as well as the date and time. Additionally, displayed interface 200 includes the location sub-area Unit 4 North 304 care metrics information 306 analyzing the current and/or prior performance of the sub-area 304. A sub-area 304 may be a nurse station within areas such as departments, units, wards, or wings of a hospital. The use of a sub-area 304 in this example is not limiting, as embodiments may focus on areas as described above or the entire hospital. The area/sub-area to be displayed may be chosen by the administrator 202 or displayed based on the administrator's location 304. Displaying care metrics information 306 associated with the sub-area 304 allows the administrator 302 to be continuously aware of the level of care being provided. The personalized care metrics 310 associated with the individual care providers may also be viewed by selecting a care provider from a care provider list. Once a name is selected the name may be displayed in field 308 and field 310 may display provider performance metrics and evaluation information such as, labor data 312, provider performance score 314 or patient satisfaction score 316, associated with the selected care provider as well as the Performance Improvement Plan 318 associated with the care provider 308. This may aid the administrator 302 when counseling the care provider 308. The provider information may represent a particular patient being cared for at a particular time, chosen by the administrator, selected by location such as when the administrator enters a room, or may be a calculated average of the care provider's patients.

In some embodiments, comments may also be displayed. Comments may be displayed as directed toward the care provider as requests by the patient, suggestions on improving performance, or preferences of the patient. The comments may be in the form of notes of the care provider on how to improve the care for a particular patient. The care provider and the administrator may view the comments independently or in tandem. Goals may be set and achievements may be met based on the comments provided by the patients, the care providers, and the administrators.

Information regarding the care provider 308 and a patient may be displayed on the device display 200. As the name of the care provider 308 is input by the administrator 302, data, such as name, time with the company, employee title, job duties, goals, achievements, shout outs, PIPs (performance improvement plans), recent performance, personal satisfaction data, patient satisfaction data, as well as any other information regarding a care provider may be displayed. Patient data may also be accessed. The results of the satisfaction data from the patient may be accessed as well as admit reason, length of stay, care provided and the provider, and all general statistics associated with the patient. Comments and suggestions may be provided by the care provider of the administrator. As an example, the different levels of information provided may be sortable by categories such as selecting a care providers, a name of a care provider, overall satisfaction score, then may be presented with a breakdown of the satisfaction score representing the patient satisfaction data and the provider satisfaction data.

Continuing in FIG. 3A, the PIP field 318 may be selected. Once an administrator 302 chooses a care provider 308, the administrator 302 may view a performance improvement plan ("PIP") by selecting box 318. A PIP may be selected from a menu of pre-generated plans, may be suggested by the system for a given care provider, unit, or issue, may be modified from a pre-generated plan, and/or may be created from scratch by an administrator or team of administrators using the application. In embodiments, attached PIPs, as well as the level of completion and progress of each PIP, may be viewed by only the administrator 302 who attached them and/or the care provider 308 or unit 304 to which the PIPs are attached and/or a subset of all administrators. Completion or progress may be given one or more benchmark dates to hit particular goals, and such completion or progress on these goals may be presented to administrators and/or care providers in symbolic, color-coded, and or graphical form.

PIPs may be presented to the care provider via display 200 in the form of a game. Goals or achievements may be presented as icons on display 200. As the goals are reached the care provider may be presented with points or any other sort of incentive. At a certain time, such as at the end of each month, an award may be presented based on the number of points accumulated by a care provider. As achievements are reached, notifications may be sent to both the care provider and one or more administrators, allowing the progress of the care provider to be easily tracked. The icons may be symbols representative of a care provider's performance, goals to meet, or achievements.

Figure 3B:
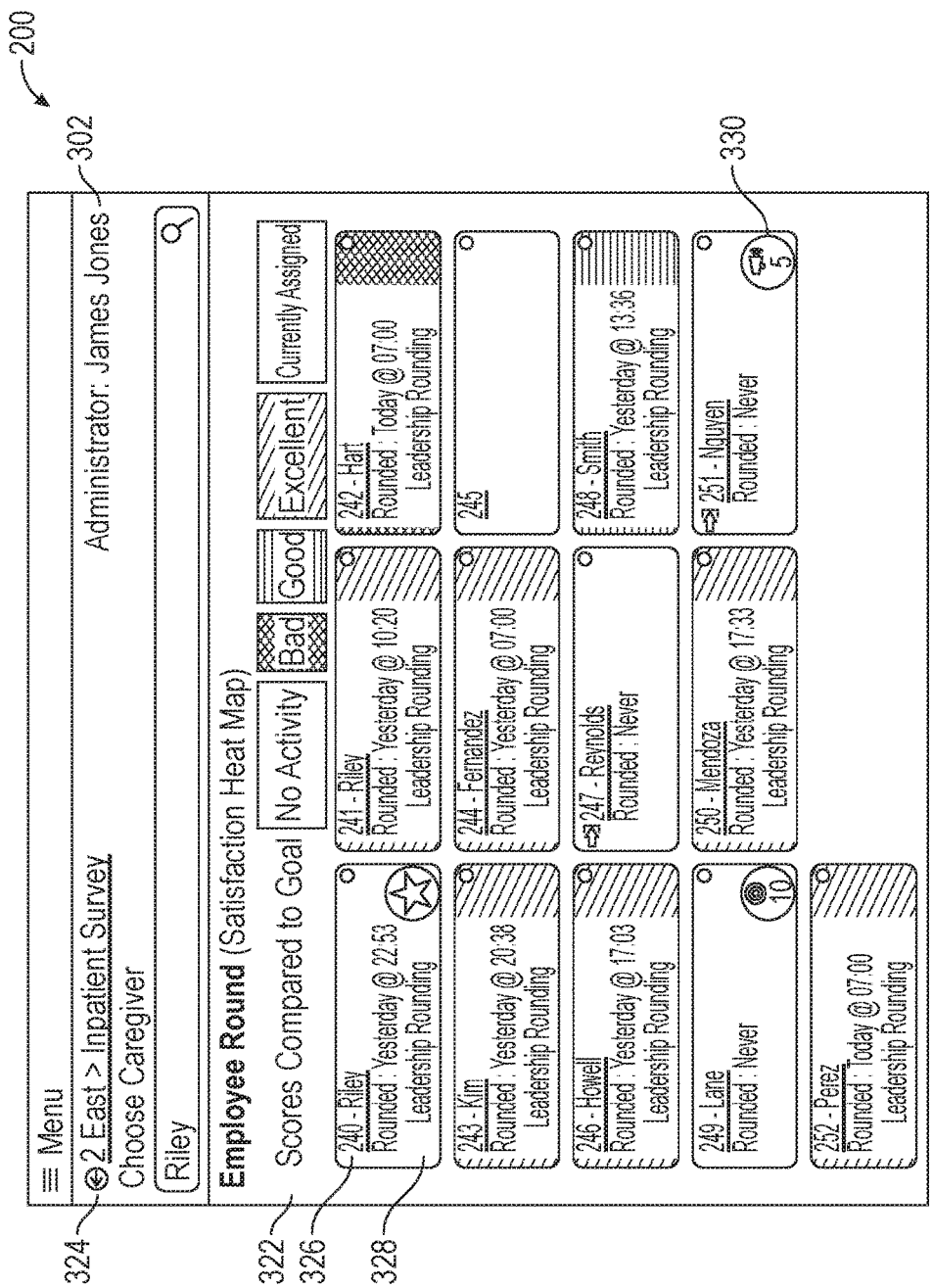

For example, symbol 330 of FIG. 3B displays a megaphone, indicating a shout out. A patient may have provided positive feedback for a care provider, resulting in the care provider receiving a megaphone icon 330. The administrator and/or the provider may also receive immediate notifications of positive feedback. Other icons may be a star reflective of an achieved goal or a target and points representing goals to reach for. In embodiments, icons may be present as any symbol reflective of any of the performance or satisfaction goals or achievements discussed herein.

The data provided by the care provider and the patient and all information related to the PIP and the evaluation of the care provider may be stored on a mobile device, on a hospital database, in a central database associated with multiple geographic locations, and/or on a personal computer in an area, sub-area, or room.

In an example, a team of administrators may log into the application at the beginning of the day and request a prioritized list of units that need a staff contact round. Based on the last recorded staff contact round and satisfaction scores of patients and providers, as well as provider performance metrics, the application may then recommend that the administrators visit Unit 4 North, a maternity and obstetrics unit. The administrators reach the maternity unit, and upon detection of arrival in the unit by their smartphones (or other mobile electronic devices), a prioritized list of care providers in that unit is displayed to the administrators as the heat map. The administrators split up and begin visiting with doctors, nurses, and technicians, reviewing performance scores, asking questions, and writing comments. As each contact is completed, the name of the provider contacted is checked off on each the prioritized list in each administrator's application, and comments become reviewable. Later, the group of administrators can meet to discuss the day's round, print reports of providers visited and unvisited, view all comments, and discuss issues and PIPs. Based on their discussions, the administrators decide to order new laundry hampers for every room in the unit, and send a message to the unit's providers that the requested change will be made. Follow-up questionnaires can be scheduled for updating progress or satisfaction score for the next week, and PIPs can be propagated by any administrator as goals are reached. The administrators may receive automatic notifications based on the scheduled appointments and updates on progress of the requested activities.

In embodiments, a PIP presents the care providers with a list of options that may be helpful in improving the care provider's performance. The care provider may also be presented with the PIP and may select an option that displays sub sections and suggested performance metrics to achieve. The suggested performance metrics may be presented as numbers with associated numbers representing the current state of the care provider's performance. As the care provider performance number gets closer to the desired number the color may go from red to yellow to green or other designated color changes, in embodiments. A box may also be displayed and checked off when the desired performance number has been met. The device may also track the history of the care provider and display achievements that have been met as well as currently pending goals that the care provider is attempting to reach.

The administrator 302 may access a care provider list, similar to the patient list 208, as depicted in FIG. 2, by selecting the field 320. A heat map of a care provider list is displayed in FIG. 3B. The care provider list 322 displays a plurality of care providers requiring counsel from administrator 302. In some embodiments, selection of a care provider from care provider list 322 may display one or more tasks to be performed by administrator 302. In embodiments, the care provider list 322 may be color coded or otherwise formatted in an attention seeking manner to display urgency of counsel requested and/or an impending time for completion of a counsel for the care provider displayed. In other embodiments only the names listed are in need of counsel and are listed in an order decided by provider performance, patient satisfaction, provider satisfaction, provider labor data, or any combination thereof. The order may be based on time since the last counsel, need of the care provider based on individual care metrics, a combination of the previously listed items, or minimizing the administrators time to complete the rounds.

Icons 330 displaying goals and achievements for each care provider may also be displayed. An icon 330 may be presented to a provider at an administrative consultation. At the consultation, a Performance Improvement Plan may be presented to the provider or the provider and administrator, or group of administrators, may develop the plan. Icons indicative of the PIP may be presented to the provider and the administrator via the display 200. In the embodiment depicted in FIG. 3B, the icons are presented to the administrator on the heat map. This may allow for immediate recognition of the progress of the care provider towards achieving the goals set out in the PIP. The icons may be presented to a care provider in any of the embodiments presented. Providing the icons to the care provider would allow the care provider to track their own progress and recognized where improvements are needed, and where the most improvements have been gained.

For example, a care provider 326 that is severely underperforming, and needs immediate counsel or has an overdue consultation, may display a red flashing light. A care provider that has been counseled recently and is performing satisfactorily may have a green light or, to save space, may not be listed. In other embodiments, only care providers that have reached a time threshold since the last counsel may appear on the display. Notifications may be automatically sent to an administrator based on the above-stated needs. This may save space and/or time for the administrator. Any care providers that have low satisfaction scores and/or low performance metrics may take priority.

Continuing with the exemplary embodiment in FIG. 3B, a heat map may be based on care provider job satisfaction score. The varying levels of scores on the list 322 may be based on feedback provided by the care provider via automated questionnaires. Since resources are not unlimited, a prioritized list of care providers in need of administrative consultation based on the care provider's job satisfaction is presented. The heat map may be based on patient satisfaction as well. A reduction in patient satisfaction may be an indicator of declining provider satisfaction. As such, the list may be prioritized by a weighted combination of both patient and care provider satisfaction. Patient satisfaction may also be weighed against performance metrics. The provider performance may decline based on the provider satisfaction and the patient satisfaction may suffer as a result. In prioritizing care provider need for administrative consultation, the combination of the three; decline in patient satisfaction, decline in provider satisfaction, and decline in provider performance, may result in a label of "Bad" on the list 322. The prioritization may be based on provider performance, patient satisfaction, provider satisfaction, provider labor data, or any weighted combination thereof.

In another exemplary embodiment, a care provider list icon for a care provider that was unable to attend a previously scheduled consultation, or for some other reason as described above having priority, may be displayed red and/or flashing to indicate that the task is overdue. Further, the care provider name may be displayed in specially formatted text, such as all capitals or bolding, to indicate that this care provider is contributing negatively to one or more sub-area/area care metrics. Additionally, or alternatively, the device displaying interface 200 may vibrate and/or generate audible alerts of urgency or criticality of help requested, in embodiments. The urgent alert may be related to a patient emergency or need. The response time of the care provider to said emergencies or needs may affect the care provider's performance metrics. The urgent alert may be related to an emergency such as a lack of staff availability or a member of the staff calling in sick. In embodiments, the alert may be in response to a high patient need, such as an unusually high patient population or a large number of critically ill patients. A replacement may be needed quickly, causing the administrator to be immediately informed via the device 200.

The collected data covered above is used to determine the care providers most in need of consultation with administrators. A scheduled round is then created that best meets the need of an administrator to perform the round and the care providers to meet with the administrator. The schedule may be based on need exclusively but may also be based on a number of other factors. These factors may include: administrator/caregiver availability, most efficient scheduling (that does not interfere with routine tasks), and avoidance of emergencies. The rounds and consultations may be performed by multiple administrators separately or as a group. The meeting times may also be based on optimizing the administrators time and location. For example, it may not be convenient or efficient to have a first meeting at one location, move to a second location for a second meeting, then return to the first location for a third meeting. The schedule may take location and time into account providing for a more optimal administrator schedule. Multiple locations may exist as the care providers may not be in the same location, as such more specific locations may be viewed in the location box 324. The schedule may also be based in part on patient feedback information from the questionnaires. All the data for determining the schedule may be used and weighted to determine an optimal schedule based on time, importance, patient feedback, performance metrics, provider labor, and provider satisfaction. The data used here is not limiting and any additional data that may be helpful in scheduling may be used.

Embodiments of the invention may facilitate cooperation between a plurality of administrators responsible for completing staff contact rounds, track identified issues, suggest performance improvement plans, and/or attach performance improvement plans to identify issues, care providers, or units as in the example above. For instance, continuing with the display in FIG. 3B one administrator 302 may be capable of creating a list of care providers 322 to receive a staff contact round on a given day and share the list with other administrators. As each administrator contacts a care provider, in some embodiments the administrator 302 may be able to mark that provider 326 as visited, or remove him/her from the list. Alternatively, or additionally, an administrator may be capable of marking uncontacted care providers or those needing a follow-up, such as with a colored dot. These markings may then be automatically or manually shared amongst administrators, visible from the day's staff contact list. The administrator upon entering an area, or manually inputting a location, may be presented with location 324, a selection of care providers 326 and tasks 328 charts on the display 200. When the location is selected, a list of tasks 328 is presented for completion within the location 324 for a giver provider 326. The list of providers 322 may list all providers for the area with icons indicating which providers are in need of consultation or the list may only present those providers in need of consultation. Once a care provider name is chosen, the care provider evaluation information, as discussed above, is presented.

The locations and times may be viewed by the care provider 302 on a care provider account. The care provider account may display only the care provider information and schedule of the care provider associated with the account. This prevents other care providers from viewing confidential information. Multiple administrators may have access to the display 200 if access to view the care provider information by the administrator is granted.

The display interface 200 in FIG. 3B also presents the care provider list 322 as a heat map. In embodiments, the heat map may be color-coded, with colors such as orange indicating that a particular care provider needs urgent attention, or other colors such as blue indicating that a care provider may have a counsel at a later date. The heat map may additionally display a set of topics to be discussed by administrator 302 and a time for consultation.

Embodiments of the invention may be capable of automatically or manually scheduling an administrator contact round between one or more administrator and one or more care provider. The application may present a visual schedule of pending staff contact rounds and/or may push notifications to care providers or administrators of upcoming or missed staff contact rounds. Care providers and administrators may request a rescheduling of a staff contact round via the application, and may be able to use the application to communicate directly via methods such as text messaging or live chat.

In some embodiments, an administrator may be able to view all known issues and/or search for issues by name, date, unit, or type. Types of issues may include training needed, insufficient resources, and communication problems. Issues may be sortable, for instance by new issues, oldest issues, worsening issues, issues with care providers that have not had a staff contact round for a given amount of time. Issues may be manually or automatically color-coded by type, severity, unit, provider type, or time. Issues may be connected to a map or other graphical representation of the responsibilities for a particular administrator.

Embodiments of the invention may store comments related to the performance or satisfaction with or from a particular care provider or unit. These responses may be free-form or may be selected from a set of pre-generated responses. Later, these comments, positive or negative, may be reviewable by administrators. Based on properties assigned to each comment or set of comments, the comments may or may not also be reviewable by associated care providers. A review of comments related to a unit or care provider may be used as one portion of a staff contact round. Access to the some or all comments by a care provider or unit may be enabled by an administrator upon initiation of a staff contact round. The comments may be incorporated into the care provider performance metrics.

In embodiments, comments may be automatically solicited. Care providers may receive questionnaires at particular times, such as at the end of a shift or just prior to breaks. The timed questionnaires may be sent based on specific tasks that have been performed such as upon completion of a patient round. The comment solicitation may also be sent when entering particular locations. The location of the care provider may be sensed automatically via location-sensing hardware. When a care provider exits an area, questions regarding the care may be supplied to the care provider's mobile device. The comments may be provided at any time and the alert system is in no way limiting.

Patients may also be able to comment on care provider performance. The patient comments may be made at will or the patient may be automatically prompted. When a care provider has attended to a patient the care provider location may be sensed or the care provider may signal that the patient has been attended, and a notification inquiring as to the level of care provided to the patient. A good rating may be sent to the care provider in the form of a "shout out". This may also be sent at the end of a patient stay when questioned about the patient's overall satisfaction. Positive and negative feedback may be automatically sent to the care provider and/or the administrator as programmed by either the administrator or the care provider.

In another exemplary embodiment, FIG. 4 depicts a maternity ward location 400 with a plurality of patient rooms 401 and a sub-area nurse station 404, and a sub-area nurse station 406. A plurality of computers 408 may be located within the nurse stations 404 and 406, providing access to accounts by care providers and administrators. A plurality of indicium devices 410 and/or electronic beacons 412 may also be located within the nurse stations.

The location-sensing component of an electronic device configured to display a graphical user interface to a care provider may automatically sense the location of care in which the care provider 414 is practicing. The location sensing may be achieved in embodiments of the invention through an electronic scan of an indicium 410. Indicium 410 may be provided as a one-dimensional or two-dimensional barcode presented on a sign mounted in a patient room 402, a sub-area 404 an area or department 400, a floor, or a hospital. Alternatively, indicium 410 may be uniquely associated with an entire clinic or a particular bed at a care location with multiple beds.

For example, a tablet computing device 418 carried by a rounding nurse may be equipped with an infrared barcode scanner. Upon scanning indicium 410, the tablet computing device captures information related to the care location 400, perhaps through consultation of a locally or remotely stored lookup table. The computing device may then use the location of care to compile a set of care tasks to be performed for one or more patients at the location of care sensed for generation of a graphical user interface 200. In embodiments, the indicium 410 indicating a location of care may be captured by a digital camera integrated into an electronic device, such as the tablet computing device or a smart phone.

In alternative embodiments, a location of care may be automatically sensed by an electronic device through establishment of a wireless connection with an electronic beacon 412. The electronic beacon 412 may be a wireless internet hub providing a Wi-Fi connection, with location of care sensed by an electronic device based on the signal strength of the Wi-Fi connection. For example, a large hospital may have a wireless internet hub for each floor in the hospital. An electronic device may sense and/or be capable of establishing a Wi-Fi connection with more than one of the internet hub electronic beacons 412. However, the nearest beacon 412, the internet hub for the floor on which the care provider is standing, will provide the strongest signal to the electronic device 418. In embodiments, the electronic device 418 may determine a location of care based on the strongest wireless internet signal available, and may thereafter generate a population of patients to be cared for at that location of care.

Alternatively, electronic beacon 412 may establish a communication link with an electronic device via Bluetooth TM or other wireless communication protocol with a limited range, and thereafter transmit to the device an identification of the location of care. These examples are not intended as limiting. Any other method of communicating wirelessly with an electronic beacon 412 to determine a location of care, such as an RFID connection, may be employed in embodiments of the invention. In alternative embodiments, a location of care may be sensed without establishing a connection with electronic beacon 310, such as through use of a Global Positioning System (GPS) or other system for determination geographic proximity. Embodiments may use any of the above methods of location determination alone or in combination and may further require manual user input.

Continuing with the exemplary embodiment depicted in FIG. 4, an administrator 420 may access one or more computers 408 or a mobile device in the maternity ward and may select an icon representing the care provider on a map and view the care provider's associated data as described above. This information may aid an administrator in scheduling a meeting with the care provider or may just allow the administrator to quickly assess the location and state of the maternity ward 400. The administrator may be able to quickly contact the care provider 414 by texting, calling, messaging, emailing, or paging the care provider via the mobile device.

Further the display may update automatically when the administrator 420 moves throughout the hospital. As the administrator 420 moves into a new section or ward, the display may update to show the map of the new area. The application may automatically update with the information for the care providers in that particular area. This may aid the administrator 420 in finding and communicating with the staff of the area. This may be performed using geo-fencing, GPS, Wi-Fi, or RFID tags.

Figure 5:
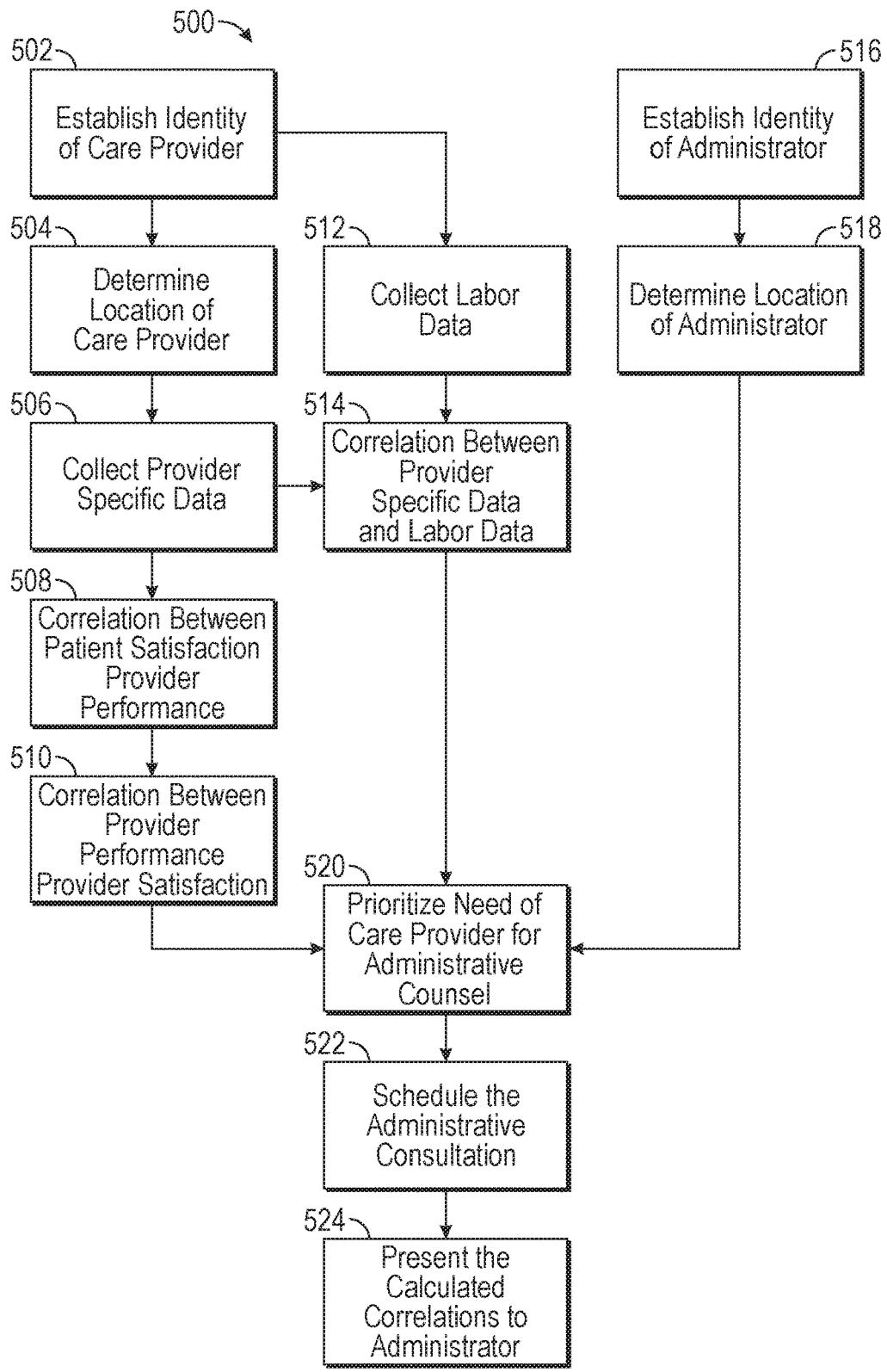
FIG. 5 depicts an exemplary flowchart illustrating the operation of a method in accordance with an embodiment of the invention.

FIG. 5 depicts a flow chart for an exemplary method 500 utilizing an automatic determination of a location of a care provider and data associated with the care provider to find correlations within the sets of data to present to an administrator. The method begins with step 502, in which an identity of a care provider is sensed. The identity may be received via indicium an indicium device and may be barcode, RFID, Bluetooth, GPS or Wi-Fi. In step 504 the location of the care provider is automatically sensed using what may be the same methods as in step 502.

The system then collects provider-specific data from a plurality of classes associated with the care provider in step 506. The classes of data may be, but are not limited to, provider performance metrics, provider satisfaction score, and patient satisfaction score.

In step 508 a correlation of the patient satisfactions score to the provider performance metric is calculated. The satisfaction of the patient may be a result of the performance metrics of the provider. The correlation of these two factors may provide an administrator with necessary tools to improve the quality of care provided to the patients. The patient satisfaction data may be collected via questionnaire.

In step 510 a correlation of the provider performance metric to the provider satisfaction data is calculated. The satisfaction of the provider may influence the level of care of the provider. This may be a motivational factor. The satisfaction of the care provider may give the administrator insight into why the performance metrics are fluctuating. The provider satisfaction data may be collected via questionnaire.

Labor data associated with the care provider is also collected in step 512. The labor data may be indicative of hours worked, duration of time on feet, or time on break. This also may include how often the care provider takes time off.

In step 514, a correlation of the provider specific data to the labor data is calculated. The provider specific data may be influenced by the labor data. This may be useful for the administrator in determining if a care provider is overworked, has a large workload or needs time off.

The identity of the administrator is determined in step 516. The identity may be received via an indicium device and may be barcode, RFID, Bluetooth, GPS or Wi-Fi. The location of the administrator is determined in step 518 by what may be the same functionality provided in step 516.

In step 520 the need of the care provider for administrative counsel is determined. As discussed before, there may be many care providers and the relative need between the care providers may result in a prioritized list based on need.

In step 522 a schedule is formulated. The schedule may be based on care provider's need for administrative counsel, the location of the care provider, the location of the administrator, the location of other care providers in need, the work load of the administrator, the work load of the care provider, time off available to a care provider, time off available to an administrator, time off taken by a care provider, time off taken by an administrator, or any combination thereof. The schedule may comprise the date and time, as well as the location, parties present, and any notes that may be helpful. The patient-specific data, labor data, and correlation results may also be presented to the care provider or administrator or both.

In step 524 the correlations are presented to the administrator. A performance improvement plan may also be automatically generated and presented as a suggestion to the administrator during this step. The schedule may be presented to the administrator in the form of rounds as described in embodiments above. The lists and or correlations results and schedule may also be presented to the care providers.

Though the plan described above is generated automatically it should be appreciated that the care provider and administrators may have full access and may alter, edit, make notes, updates, and/or influence the schedule at will.

The preceding steps of FIG. 5 may be performed in any order and some steps may be omitted as allowable to still achieve a desired result. For example, if the desired result is to find a correlation between the provider satisfaction data and provider performance metrics, then it is not necessary to spend the extra power to collect and correlate labor data, or determine the correlation between provider performance and provider satisfaction. Any combination of collecting data and correlating data may be achieved for a desired result.

In another exemplary embodiment, the administrator may be alerted of an emergency via the device 200. The device normal mode, running as described above, may be interrupted, for example, by a government body such as the National Weather Service in the United States. The alert may be warning of a tornado, flood, hurricane or other danger that may be issued online. The alert may also be representative of a warning of a dangerous person or persons in the area, vehicle thefts, criminal activity, a fire, or any other local emergency and may be issued by hospital security. The alert may be from a federal agency such as the National Weather Service, Homeland Security, the Federal Emergency Management Agency, or the Federal Bureau of Investigation. The alert may provide instructions to the administrator to lock down the facility or specified areas. The alert also may provide information for evacuating the building or moving patients/staff to a secure or safe location.

Any and all data, events, care providers, patients, administrators, locations, comments, and conversations may be automatically documented for future reference.

It should be appreciated that, while the above disclosure is directed mainly to the field of medical software, some embodiments of the invention may be employed with other uses. Examples of facilities likely to make use of embodiments of the invention include Doctors' Offices, Emergency Departments, Inpatient and Outpatient Clinics, Rehabilitation and Recovery Units, Long Term Nursing Care Facilities, and Home Health Services, but are not limited to these. Embodiments of the invention may be used in any setting to track any type of staff review rounds, and may be used in medical facilities for non-care providers, such as maintenance teams. Embodiments of the invention may be used in non-medical settings, such as manufacturing. Such embodiments may utilize real-time location sensing structures in tandem with wearables and appliances, like pedometers and fabrication equipment, to monitor and manage staffing, workflow, and productivity in an industrial environment. The medical field discussed is merely exemplary and should not be construed as limiting.

The invention claimed is:

1. A system of presenting a graphical user interface for presenting rounds for a plurality of administrators, the system comprising;
    a processor;
    an identity input component;
    a location sensing component; and
    a non-transitory computer readable medium storing computer-executable instructions which, when executed by the processor, perform the steps of:
        establishing an identity of a care provider via the identity input component;
        establishing an identity of an administrator via the identity input component;
        sensing a location of the care provider via the location sensing component;
        sensing a location of the administrator via the location sensing component;
        collecting provider specific data from a plurality of data classes,
    wherein the plurality of data classes includes a provider performance metric, a satisfaction score of the care provider, and a satisfaction score of a patient of the care provider;
        collecting labor data for the care provider;
        calculating a correlation of the patient satisfaction score to the provider performance metric;
        calculating a correlation of the provider performance metric to the provider satisfaction score;
        calculating a correlation of the provider-specific data from each data class to the labor data;
        prioritizing a need of the care provider for administrative consultation based on the location of the administrator, the location of the care provider, and the provider-specific data;
        scheduling the administrative consultation; and
        presenting the calculated correlations to the administrator for the administrative consultation.

2. The system of claim 1, wherein the location of the care providers is sensed by Wi-Fi.

3. The system of claim 1, wherein the provider performance metric is at least partially collected using a mobile device associated with the care provider.

4. The system of claim 3, wherein the provider performance metric is at least partially collected by accelerometers on the mobile device.

5. The system of claim 1, wherein the patient satisfaction score is determined at least in part by a response to a questionnaire completed by the patient.

6. The system of claim 1, wherein the labor data at least partially comprises hours worked.

7. The system of claim 1, wherein the step of prioritizing comprises comparing the need of a care provider for administrative consultation at a location to the need of other care providers for administrative consultation at the same location.

8. A method of facilitating an administrative consultation between a care provider and an administrator, comprising the steps of:
    sensing a location of the care provider;
    collecting provider-specific data from a plurality of data classes, wherein the plurality of data classes includes a provider performance metric, a satisfaction score of the care provider, and a satisfaction score of a patient of the care provider;
    collecting labor data for the care provider;
    calculating a correlation of the provider-specific data from each data class to the labor data;
    prioritizing a need of the care provider for administrative consultation based on the location of the administrator, the location of the care provider, and the provider-specific data;
    scheduling the administrative consultation; and
    presenting the calculated correlation and the plurality of data classes to the administrator for the administrative consultation.

9. The method of claim 8, further comprising calculating a correlation of the patient satisfaction score to the provider performance metric.

10. The method of claim 8, further comprising calculating a correlation of the provider performance metric to the provider satisfaction score.

11. The method of claim 8, wherein the satisfaction score of the care provider is determined at least in part by a response to a questionnaire completed by the care provider.

12. The method of claim 8, further comprising notifying the administrator when an emergency or need is detected.

13. The method of claim 12, wherein the emergency is an alert from a federal agency.

14. The method of claim 8, wherein the provider performance metric of the care provider is determined at least in part based on the response time to a patient emergency or need.

15. A method of facilitating an administrative consultation between a care provider and an administrator, comprising the steps of:
    sensing a location of the care provider;
    sensing a location of the administrator;
    collecting provider-specific data from a plurality of data classes, wherein the plurality of data classes includes a provider performance metric, a satisfaction score of the care provider, and a satisfaction score of a patient of the care provider;
    collecting labor data for the care provider;
    calculating a correlation of the patient satisfaction score to the provider performance metric;
    calculating a correlation of the provider performance metric to the provider satisfaction score;
    calculating a correlation of the provider-specific data from each data class to the labor data;

prioritizing a need of the care provider for administrative consultation based on the location of the administrator, the location of the care provider, and the provider-specific data;
scheduling the administrative consultation; and
presenting the calculated correlation to the administrator for the administrative consultation.

16. The method of claim 15, wherein the administrator is notified of care providers in need of counsel based on the location of the administrator.

17. The method of claim 15,
further comprising presenting the care provider a list of performance goals to achieve,
wherein the performance goals are based on a patient's satisfaction feedback.

18. The method of claim 15,
further comprising presenting the administrator a list of performance goals of the care provider;
wherein the performance goals of the care provider are based on the care provider's satisfaction feedback.

19. The method of claim 15, wherein the schedule comprises a time, a date, a location, and the names of all parties to attend.

20. The method of claim 15, wherein the step of prioritizing comprises comparing the need of the care provider for administrative consultation at a location to the need of other care providers for administrative consultation at a different location.

* * * * *